(12) United States Patent
Robinson et al.

(10) Patent No.: US 11,365,490 B2
(45) Date of Patent: *Jun. 21, 2022

(54) THERMAL CUTTING ELEMENTS, ELECTROSURGICAL INSTRUMENTS INCLUDING THERMAL CUTTING ELEMENTS, AND METHODS OF MANUFACTURING

(71) Applicant: Covidien LP, Mansfield, MA (US)

(72) Inventors: William Robinson, Boulder, CO (US); James D. Allen, IV, Broomfield, CO (US); Mark A. Johnston, Boulder, CO (US); Brendan J. Heinig, Boulder, CO (US); Hector A. MacPherson, Denver, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/102,315

(22) Filed: Nov. 23, 2020

(65) Prior Publication Data
US 2021/0189583 A1    Jun. 24, 2021

Related U.S. Application Data

(60) Provisional application No. 62/952,232, filed on Dec. 21, 2019, provisional application No. 62/952,234, filed on Dec. 21, 2019.

(51) Int. Cl.
*C25D 11/02* (2006.01)
*A61B 18/08* (2006.01)
(Continued)

(52) U.S. Cl.
CPC ............ *C25D 11/02* (2013.01); *A61B 18/085* (2013.01); *B21D 22/02* (2013.01); *B41M 1/12* (2013.01);
(Continued)

(58) Field of Classification Search
None
See application file for complete search history.

(56) References Cited

U.S. PATENT DOCUMENTS 2,068,721 A    1/1937    Wappler
4,091,813 A    5/1978    Shaw et al.
(Continued)

FOREIGN PATENT DOCUMENTS

EP    2754403 A2    7/2014

OTHER PUBLICATIONS

Gnedenkov et al., "Magnesium fabricated using additive technology: Specificity of corrosion and protection", Journal of Alloys and Compounds, Elsevier, vol. 808, Jul. 29, 2019, XP085792710.
(Continued)

*Primary Examiner* — Wojciech Haske
(74) *Attorney, Agent, or Firm* — Carter, DeLuca & Farrell LLP

(57) ABSTRACT

A method of manufacturing a thermal cutting element for a surgical instrument includes manufacturing a substrate, coating at least a portion of the substrate via Plasma Electrolytic Oxidation (PEO), and disposing a heating element on at least a portion of the PEO-coated substrate. The method may further include attaching the thermal cutting element to a jaw member of a surgical instrument.

20 Claims, 8 Drawing Sheets

(51) Int. Cl.
  B21D 22/02   (2006.01)
  B41M 1/12    (2006.01)
  B41M 3/00    (2006.01)
  C23C 14/02   (2006.01)
  C23C 14/04   (2006.01)
  C23C 14/34   (2006.01)
  C23C 28/00   (2006.01)
  A61B 17/00   (2006.01)
  A61B 18/00   (2006.01)

(52) U.S. Cl.
  CPC ........... *B41M 3/006* (2013.01); *C23C 14/024* (2013.01); *C23C 14/042* (2013.01); *C23C 14/34* (2013.01); *C23C 28/345* (2013.01); *A61B 2017/00526* (2013.01); *A61B 2018/0063* (2013.01); *A61B 2018/00077* (2013.01); *A61B 2018/00083* (2013.01); *A61B 2018/00107* (2013.01); *A61B 2018/00178* (2013.01); *A61B 2018/00589* (2013.01); *A61B 2018/00595* (2013.01)

(56) References Cited

U.S. PATENT DOCUMENTS

| | | |
|---|---|---|
| 5,389,098 A | 2/1995 | Tsuruta et al. |
| 5,403,312 A | 4/1995 | Yates et al. |
| 5,465,895 A | 11/1995 | Knodel et al. |
| 5,810,811 A | 9/1998 | Yates et al. |
| 5,827,271 A | 10/1998 | Buysse et al. |
| 5,833,690 A | 11/1998 | Yates et al. |
| 5,876,401 A | 3/1999 | Schulze et al. |
| 5,911,719 A | 6/1999 | Eggers |
| 6,024,741 A | 2/2000 | Williamson, IV et al. |
| 6,086,586 A | 7/2000 | Hooven |
| 6,273,887 B1 | 8/2001 | Yamauchi et al. |
| 6,402,747 B1 | 6/2002 | Lindemann et al. |
| 6,602,252 B2 | 8/2003 | Mollenauer |
| 6,736,813 B2 | 5/2004 | Yamauchi et al. |
| 6,776,780 B2 | 8/2004 | Mulier et al. |
| 6,802,843 B2 | 10/2004 | Truckai et al. |
| 6,808,525 B2 | 10/2004 | Latterell et al. |
| 6,821,273 B2 | 11/2004 | Mollenauer |
| 6,860,880 B2 | 3/2005 | Treat et al. |
| 6,899,710 B2 | 5/2005 | Hooven |
| 6,929,641 B2 | 8/2005 | Goble et al. |
| 6,953,461 B2 | 10/2005 | McClurken et al. |
| 7,011,656 B2 | 3/2006 | McGaffigan et al. |
| 7,033,356 B2 | 4/2006 | Latterell et al. |
| 7,070,597 B2 | 7/2006 | Truckai et al. |
| 7,083,619 B2 | 8/2006 | Truckai et al. |
| 7,112,201 B2 | 9/2006 | Truckai et al. |
| 7,125,409 B2 | 10/2006 | Truckai et al. |
| 7,147,637 B2 | 12/2006 | Goble |
| 7,169,146 B2 | 1/2007 | Truckai et al. |
| 7,204,835 B2 | 4/2007 | Latterell et al. |
| 7,270,664 B2 | 9/2007 | Johnson et al. |
| 7,276,068 B2 | 10/2007 | Johnson et al. |
| 7,326,202 B2 | 2/2008 | McGaffigan |
| 7,329,255 B2 | 2/2008 | McGaffigan |
| 7,354,440 B2 | 4/2008 | Truckal et al. |
| 7,357,802 B2 | 4/2008 | Palanker et al. |
| 7,364,577 B2 | 4/2008 | Wham et al. |
| 7,396,356 B2 | 7/2008 | Mollenauer |
| 7,419,490 B2 | 9/2008 | Falkenstein et al. |
| 7,686,827 B2 | 3/2010 | Hushka |
| 7,815,641 B2 | 10/2010 | Dodde et al. |
| 7,931,649 B2 | 4/2011 | Couture et al. |
| 8,034,051 B2 | 10/2011 | Martin et al. |
| 8,162,940 B2 | 4/2012 | Johnson et al. |
| 8,187,273 B2 | 5/2012 | Kerr et al. |
| 8,197,472 B2 | 6/2012 | Lau et al. |
| 8,226,649 B2 | 7/2012 | Falkenstein et al. |
| 8,292,879 B2 | 10/2012 | Manwaring et al. |
| 8,303,585 B2 | 11/2012 | Mollenauer |
| 8,372,066 B2 | 2/2013 | Manwaring et al. |
| 8,377,052 B2 | 2/2013 | Manwaring et al. |
| 8,394,094 B2 | 3/2013 | Edwards et al. |
| 8,425,503 B2 | 4/2013 | Manwaring et al. |
| 8,491,578 B2 | 7/2013 | Manwaring et al. |
| 8,491,626 B2 | 7/2013 | Roy et al. |
| 8,523,850 B2 | 9/2013 | Manwaring et al. |
| 8,523,852 B2 | 9/2013 | Manwaring et al. |
| 8,551,088 B2 | 10/2013 | Falkenstein et al. |
| 8,562,598 B2 | 10/2013 | Falkenstein et al. |
| 8,568,411 B2 | 10/2013 | Falkenstein et al. |
| 8,597,293 B2 | 12/2013 | Falkenstein et al. |
| 8,597,297 B2 | 12/2013 | Couture et al. |
| 8,617,151 B2 | 12/2013 | Denis et al. |
| 8,623,003 B2 | 1/2014 | Lau et al. |
| 8,636,730 B2 | 1/2014 | Keppel |
| 8,734,445 B2 | 5/2014 | Johnson et al. |
| 8,915,909 B2 | 12/2014 | Manwaring et al. |
| 8,932,279 B2 | 1/2015 | Stringham et al. |
| 8,951,248 B2 | 2/2015 | Messerly et al. |
| 9,005,199 B2 | 4/2015 | Beckman et al. |
| 9,039,694 B2 | 5/2015 | Ross et al. |
| 9,050,100 B2 | 6/2015 | Fates et al. |
| 9,084,606 B2 | 7/2015 | Greep |
| 9,131,977 B2 | 9/2015 | Manwaring et al. |
| 9,149,321 B2 | 10/2015 | Stringham et al. |
| 9,192,427 B2 | 11/2015 | Johnson et al. |
| 9,265,553 B2 | 2/2016 | Manwaring et al. |
| 9,265,554 B2 | 2/2016 | Manwaring et al. |
| 9,265,555 B2 | 2/2016 | Manwaring et al. |
| 9,265,556 B2 | 2/2016 | Manwaring et al. |
| 9,320,560 B2 | 4/2016 | Manwaring et al. |
| 9,387,037 B2 | 7/2016 | Yang |
| 9,402,679 B2 | 8/2016 | Ginnebaugh et al. |
| 9,579,146 B2 | 2/2017 | Johnson et al. |
| 9,918,774 B2 | 3/2018 | Batchelor et al. |
| 9,931,157 B2 | 4/2018 | Strobl et al. |
| 9,955,858 B2 | 5/2018 | Pamnani et al. |
| 10,085,794 B2 | 10/2018 | Kerr et al. |
| 10,204,773 B2 | 2/2019 | Sugiyama et al. |
| 10,213,247 B2 | 2/2019 | Manwaring et al. |
| 2007/0135808 A1 | 6/2007 | Kupferschmid et al. |
| 2007/0265616 A1 | 11/2007 | Couture et al. |
| 2008/0086195 A1 | 4/2008 | Atanasoka et al. |
| 2008/0257585 A1* | 10/2008 | Morse ............... C25D 11/026 174/252 |
| 2012/0226270 A1 | 9/2012 | Manwaring et al. |
| 2014/0135804 A1 | 5/2014 | Weisenburgh, II et al. |
| 2017/0156788 A1 | 6/2017 | Johnson et al. |
| 2017/0196648 A1 | 7/2017 | Ward et al. |
| 2018/0206907 A1* | 7/2018 | Dycus ............... A61B 18/085 |
| 2018/0303322 A1 | 10/2018 | Pamnani et al. |
| 2019/0000538 A1 | 1/2019 | Widenhouse et al. |
| 2019/0262062 A1 | 8/2019 | Akagane |

OTHER PUBLICATIONS

International Search Report and Written Opinion issued in corresponding International Application No. PCT/US2020/061998 dated Mar. 22, 2021, 14 pages.

* cited by examiner

THERMAL CUTTING ELEMENTS, ELECTROSURGICAL INSTRUMENTS INCLUDING THERMAL CUTTING ELEMENTS, AND METHODS OF MANUFACTURING

CROSS-REFERENCE TO RELATED APPLICATIONS

This application claims the benefit of, and priority to, U.S. Provisional Patent Application Nos. 62/952,232 and 62/952,234, both filed on Dec. 21, 2019, the entire contents of each of which are hereby incorporated herein by reference.

FIELD

The present disclosure relates to surgical instruments and, more particularly, to thermal cutting elements, electrosurgical instruments including thermal cutting elements, and methods of manufacturing thermal cutting elements.

BACKGROUND

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife that is advanced between the jaw members to cut the treated tissue. As an alternative to a mechanical knife, an energy-based tissue cutting element may be provided to cut the treated tissue using energy, e.g., thermal, electrosurgical, ultrasonic, light, or other suitable energy.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with aspects of the present disclosure is a thermal cutting element for a surgical instrument. The thermal cutting element includes a substrate, a Plasma Electrolytic Oxidation (PEO) coating disposed on the substrate, and a heating element disposed on the PEO coating and including first and second end portions adapted to connect to different potentials of electrical energy to heat the heating element.

In an aspect of the present disclosure, the heating element defines a continuous circuit trace between the first and second end portions.

In another aspect of the present disclosure, the first and second end portions of the heating element are disposed adjacent one another.

In still another aspect of the present disclosure, first and second electrical contacts are disposed on the respective first and second end portions of the heating element. The first and second electrical contacts are configured to facilitate connection of the different potentials of electrical energy to the first and second end portions, respectively.

In yet another aspect of the present disclosure, the substrate is formed from aluminum, titanium, an aluminum alloy, or a titanium alloy.

In still yet another aspect of the present disclosure, the PEO coating defines an average thickness of about 50 micrometers to about 150 micrometers; in other aspects, about 75 micrometers to about 125 micrometers; in other aspects about 100 micrometers.

In another aspect of the present disclosure, the substrate defines an elongated body and a proximal connection flange extending from the elongated body. The first and second end portions of the heating element are disposed at the proximal connection flange.

A jaw member of a surgical instrument provided in accordance with the present disclosure includes a structural frame including a proximal flange portion and a distal body portion, a jaw housing surrounding the distal body portion of the structural frame, and a tissue-treating plate disposed atop the jaw housing. The tissue-treating plate defines a longitudinal slot therethrough along at least a portion of a length thereof. The jaw member further includes a thermal cutting element disposed within the jaw housing and extending through at least a portion of the longitudinal slot along at least a portion of a length of the tissue-treating plate. The thermal cutting element may be configured similar to any of the aspects detailed above or otherwise provided herein.

In aspects, the tissue-treating plate is formed from an electrically-conductive material and is adapted to connect to a source of electrosurgical energy. In such aspects, the tissue-treating plate is electrically isolated from the heating element.

In aspects, the thermal cutting element includes an attachment flange extending therefrom into the jaw housing. The attachment flange facilitates attachment of the thermal cutting element within the jaw housing.

A method of manufacturing a thermal cutting element for a surgical instrument provided in accordance with aspects of the present disclosure includes manufacturing a substrate, coating at least a portion of the substrate via Plasma Electrolytic Oxidation (PEO), and disposing a heating element on at least a portion of the PEO-coated substrate.

In an aspect of the present disclosure, disposing the heating element includes forming a continuous circuit trace on the PEO-coated substrate. The continuous circuit trace may extend between first and second end portions of the heating element. In aspects, forming the continuous circuit trace on the PEO-coated substrate includes forming a circuit trace pattern wherein first and second end portions of the circuit trace pattern are disposed adjacent one another.

In another aspect of the present disclosure, disposing the heating element includes sputtering the heating element onto the PEO-coated substrate.

In still another aspect of the present disclosure, disposing the heating element includes screen printing the heating element onto the PEO-coated substrate.

In yet another aspect of the present disclosure, the method further includes disposing first and second electrical contacts on respective first and second end portions of the heating element. Disposing the first and second electrical contacts may be accomplished via sputtering, screen printing, or other suitable method.

In another aspect of the present disclosure, manufacturing the substrate includes die-stamping the substrate. In aspects, the substrate is one of a plurality of substrates progressively-die stamped from a carrier strip.

In yet another aspect of the present disclosure, the method further includes disposing an electrically insulative material on at least a portion of the heating element.

In aspects of the present disclosure, the PEO is controlled such that the PEO coating defines an average thickness of about 50 micrometers to about 150 micrometers; in other aspects, about 75 micrometers to about 125 micrometers; and, in still other aspects, about 100 micrometers.

In another aspect of the present disclosure, the method further includes attaching the heating element-disposed, PEO-coated substrate to a jaw member.

Attaching the heating element-disposed, PEO-coated substrate to the jaw member, in aspects, includes electrically coupling first and second end portions of the heating element to first and second electrical connectors, respectively, and/or mechanically coupling an attachment flange of the substrate to a jaw housing of the jaw member. The mechanical coupling may include overmolding the jaw housing to the attachment flange.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
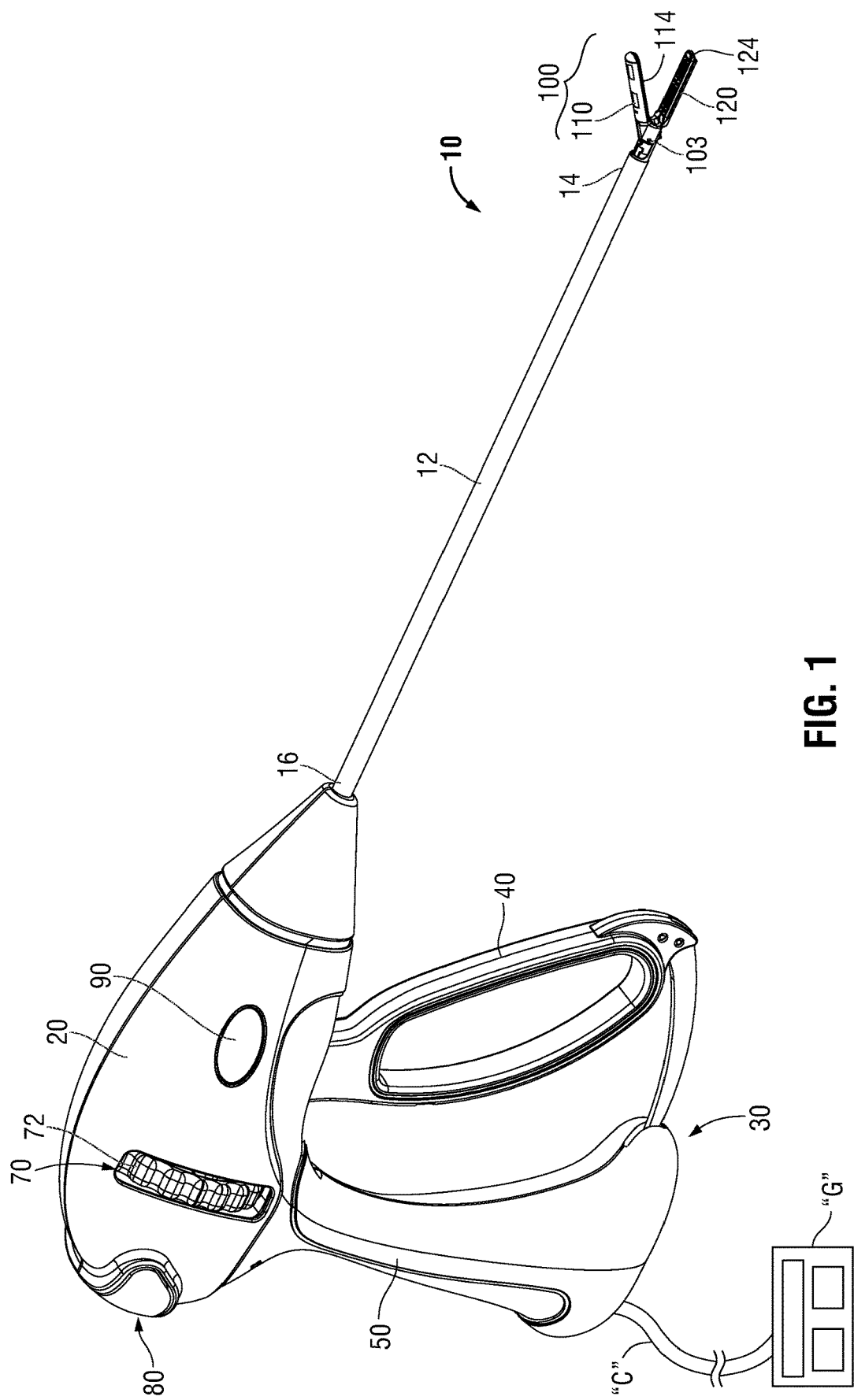
FIG. 1 is a perspective view of a shaft-based electrosurgical forceps provided in accordance with the present disclosure shown connected to an electrosurgical generator.

Referring to FIG. 1, a shaft-based electrosurgical forceps provided in accordance with the present disclosure is shown generally identified by reference numeral 10. Aspects and features of forceps 10 not germane to the understanding of the present disclosure are omitted to avoid obscuring the aspects and features of the present disclosure in unnecessary detail.

Forceps 10 includes a housing 20, a handle assembly 30, a trigger assembly 60, a rotating assembly 70, a first activation switch 80, a second activation switch 90, and an end effector assembly 100. Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable "C" that connects forceps 10 to an energy source, e.g., an electrosurgical generator "G." Cable "C" includes a wire (or wires) (not shown) extending therethrough that has sufficient length to extend through shaft 12 in order to connect to one or both tissue-treating surfaces 114, 124 of jaw members 110, 120, respectively, of end effector assembly 100 (see FIG. 4) to provide energy thereto. First activation switch 80 is coupled to tissue-treating surfaces 114, 124 (FIG. 4) and the electrosurgical generator "G" for enabling the selective activation of the supply of energy to jaw members 110, 120 for treating, e.g., cauterizing, coagulating/desiccating, and/or sealing, tissue. Second activation switch 90 is coupled to thermal cutting element 130 of jaw member 120 (FIG. 4) and the electrosurgical generator "G" for enabling the selective activation of the supply of energy to thermal cutting element 150 for thermally cutting tissue.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced-apart position and an approximated position to grasp tissue between tissue-treating surfaces 114, 124 of jaw members 110, 120. As shown in FIG. 1, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110, 120. Rotating assembly 70 includes a rotation wheel 72 that is selectively rotatable in either direction to correspondingly rotate end effector assembly 100 relative to housing 20.

Figure 2:
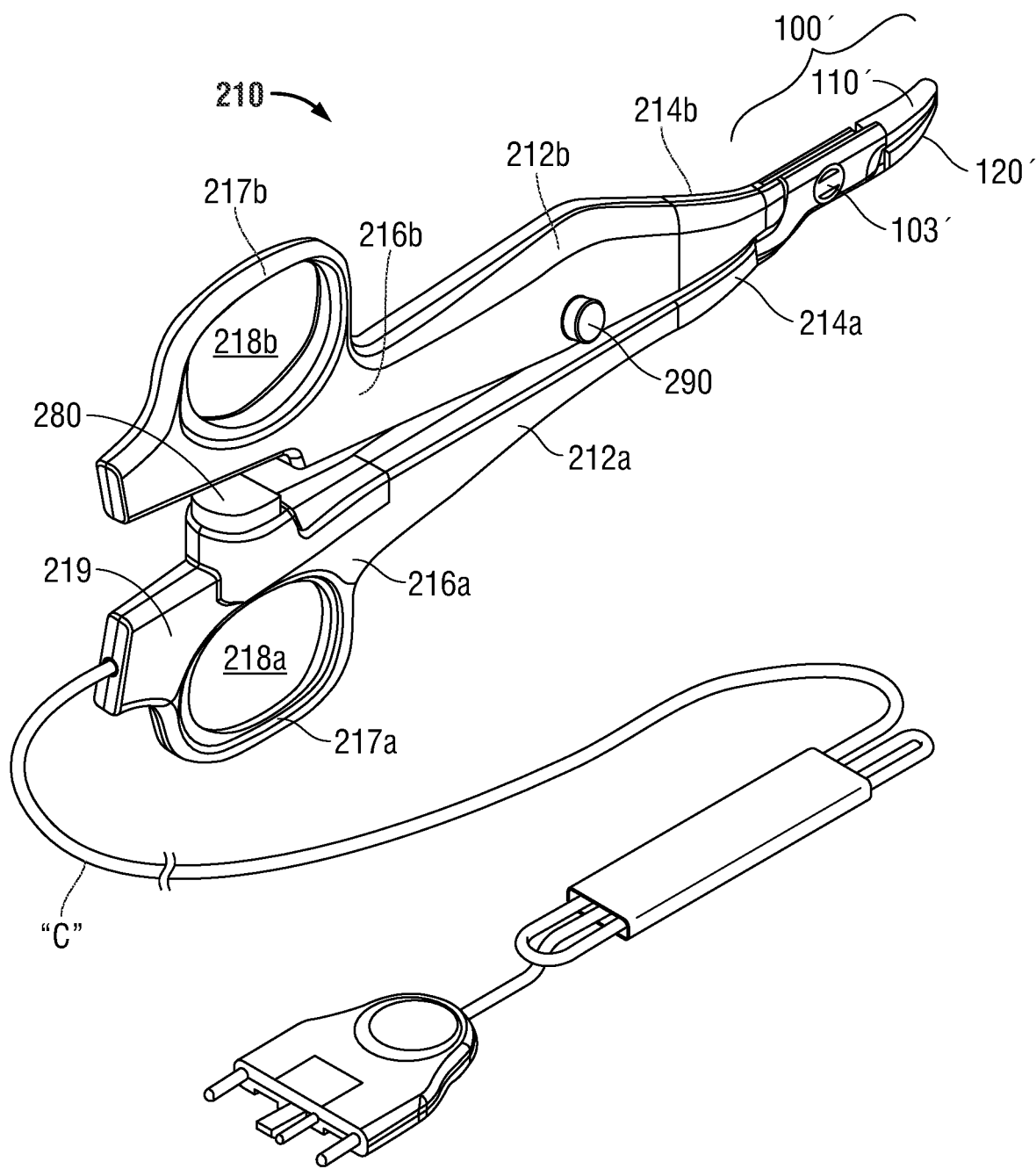
FIG. 2 is a perspective view of a hemostat-style electrosurgical forceps provided in accordance with the present disclosure.

Referring to FIG. 2, a hemostat-style electrosurgical forceps provided in accordance with the present disclosure is shown generally identified by reference numeral 210. Aspects and features of forceps 210 not germane to the understanding of the present disclosure are omitted to avoid obscuring the aspects and features of the present disclosure in unnecessary detail.

Figure 4:
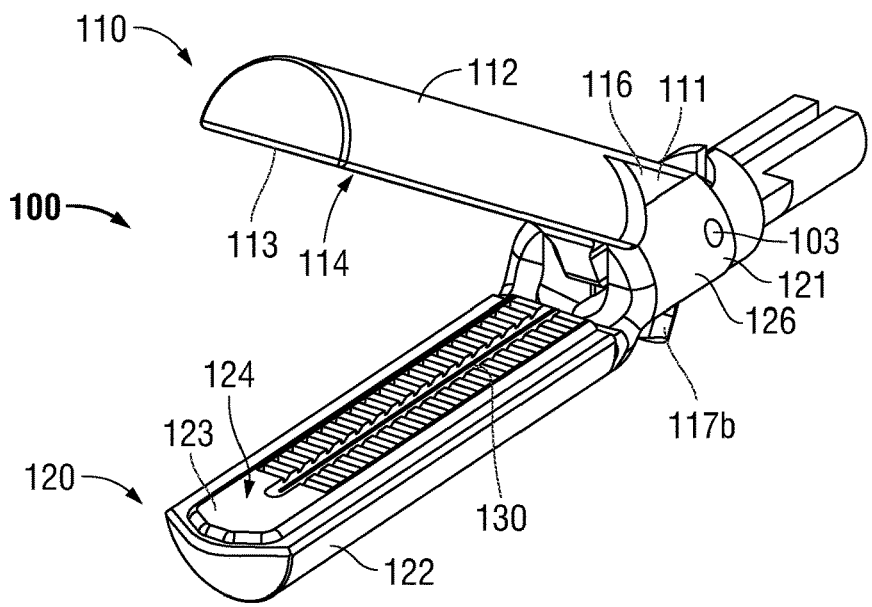
FIG. 4 is a perspective view of a distal end portion of the forceps of FIG. 1, wherein first and second jaw members of an end effector assembly of the forceps are disposed in a spaced-apart position.

Forceps 210 includes two elongated shaft members 212a, 212b, each having a proximal end portion 216a, 216b, and a distal end portion 214a, 214b, respectively. Forceps 210 is configured for use with an end effector assembly 100' similar to end effector assembly 100 (FIG. 4). More specifically, end effector assembly 100' includes first and second jaw members 110', 120' attached to respective distal end portions 214a, 214b of shaft members 212a, 212b. Jaw members 110', 120' are pivotably connected about a pivot 103'. Each shaft member 212a, 212b includes a handle 217a, 217b disposed at the proximal end portion 216a, 216b thereof. Each handle 217a, 217b defines a finger hole 218a, 218b therethrough for receiving a finger of the user. As can be appreciated, finger holes 218a, 218b facilitate movement of the shaft members 212a, 212b relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shaft members 212a, 212b of forceps 210, e.g., shaft member 212b, includes a proximal shaft connector 219 configured to connect forceps 210 to a source of energy, e.g., electrosurgical generator "G" (FIG. 1). Proximal shaft connector 219 secures a cable "C" to forceps 210 such that the user may selectively supply energy to jaw members 110', 120' for treating tissue. More specifically, a first activation switch 280 is provided for supplying energy to jaw members 110', 120' to treat tissue upon sufficient approximation of shaft members 212a, 212b, e.g., upon activation of first activation switch 280 via shaft member 212a. A second activation switch 290 disposed on either or both of shaft members 212a, 212b is coupled to the thermal cutting element (not shown, similar to thermal cutting element 150 of jaw member 120 (FIG. 4)) of one of the jaw members 110', 120' of end effector assembly 100' and to the electrosurgical generator "G" for enabling the selective activation of the supply of energy to the thermal cutting element for thermally cutting tissue.

Jaw members 110', 120' define a curved configuration wherein each jaw member is similarly curved laterally off of a longitudinal axis of end effector assembly 100'. However, other suitable curved configurations including curvature towards one of the jaw members 110, 120' (and thus away from the other), multiple curves with the same plane, and/or multiple curves within different planes are also contemplated. Jaw members 110, 120 of end effector assembly 100 (FIG. 1) may likewise be curved according to any of the configurations noted above or in any other suitable manner.

Figure 3:
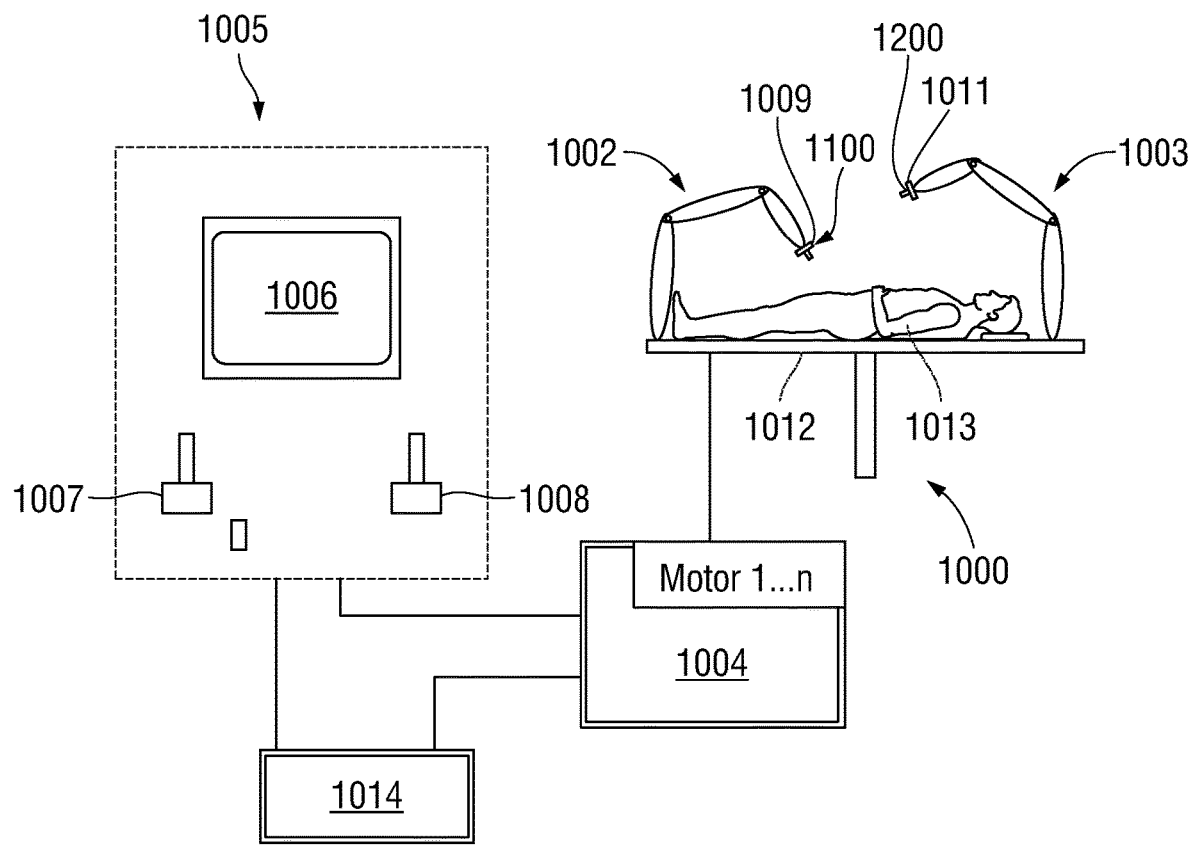
FIG. 3 is a schematic illustration of a robotic surgical instrument provided in accordance with the present disclosure.

Referring to FIG. 3, a robotic surgical instrument provided in accordance with the present disclosure is shown generally identified by reference numeral 1000. Aspects and features of robotic surgical instrument 1000 not germane to the understanding of the present disclosure are omitted to avoid obscuring the aspects and features of the present disclosure in unnecessary detail.

Robotic surgical instrument 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode. Robotic surgical instrument 1000 may be configured for use on a patient 1013 lying on a patient table 1012 to be treated in a minimally invasive manner. Robotic surgical instrument 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100 is similar to end effector assembly 100 (FIG. 4), although other suitable end effector assemblies for coupling to attaching device 1009 are also contemplated. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Figure 5A:
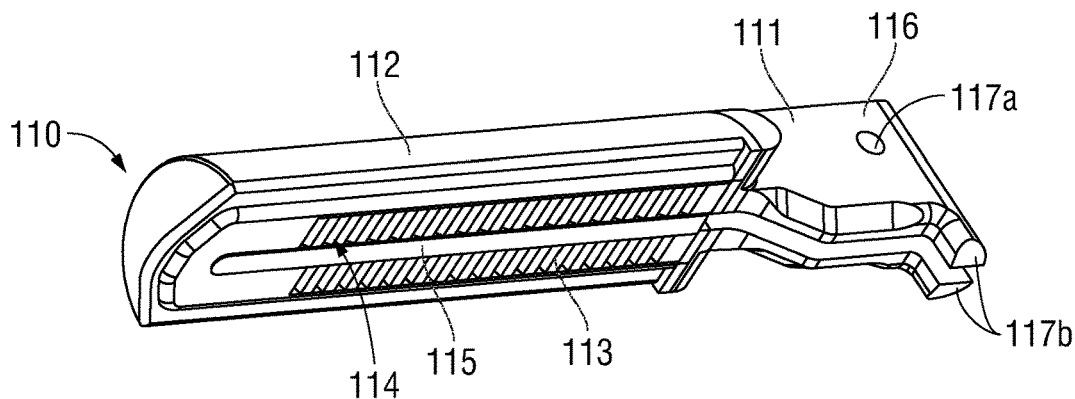
FIG. 5A is a bottom, perspective view of the first jaw member of the end effector assembly of FIG. 4.
Figure 5B:
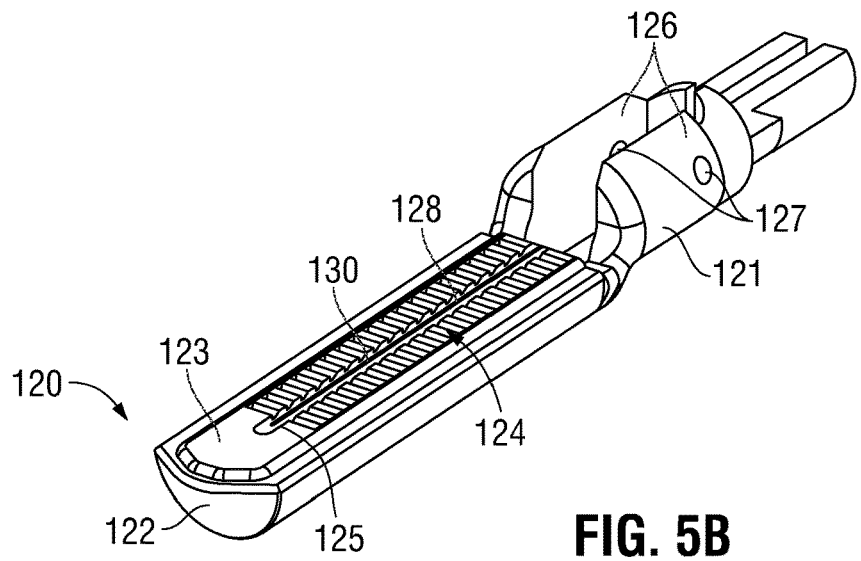
FIG. 5B is a top, perspective view of the second jaw member of the end effector assembly of FIG. 4.

Turning to FIGS. 4-5B, end effector assembly 100, as noted above, includes first and second jaw members 110, 120. Each jaw member 110, 120 may include a structural frame 111, 121, a jaw housing 112, 122, and a tissue-treating plate 113, 123 defining the respective tissue-treating surface 114, 124 thereof. Alternatively, only one of the jaw members, e.g., jaw member 120, may include a structural frame 121, jaw housing 122, and tissue-treating plate 123 defining the tissue-treating surface 124. In such embodiments, the other jaw member, e.g., jaw member 110, may be formed as a single unitary body, e.g., a piece of conductive material acting as the structural frame 111 and jaw housing 112 and defining the tissue-treating surface 114. An outer surface of the jaw housing 112, in such embodiments, may be at least partially coated with an insulative material or may remain exposed. In embodiments, tissue-treating plates 113, 123 may be deposited onto jaw housings 112, 122 or jaw inserts (not shown) disposed within jaw housings 112, 122, e.g., via sputtering. Alternatively, tissue-treating plates 113, 123 may be pre-formed and engaged with jaw housings 112, 122 and/or jaw inserts (not shown) disposed within jaw housings 112, 122 via, for example, overmolding, adhesion, mechanical engagement, etc.

Referring in particular to FIGS. 4 and 5A, jaw member 110, as noted above, may be configured similarly as jaw member 120, may be formed as a single unitary body, or may be formed in any other suitable manner so as to define a structural frame 111 and a tissue-treating surface 114 opposing tissue-treating surface 124 of jaw member 120. Structural frame 111 includes a proximal flange portion 116 about which jaw member 110 is pivotably coupled to jaw member 120. In shaft-based or robotic embodiments, proximal flange portion 116 may further include an aperture 117a for receipt of pivot 103 and at least one protrusion 117b extending therefrom that is configured for receipt within an aperture defined within a drive sleeve of the drive assembly (not shown) such that translation of the drive sleeve, e.g., in response to actuation of movable handle 40 (FIG. 1) or a robotic drive, pivots jaw member 110 about pivot 103 and relative to jaw member 120 between the spaced-apart position and the approximated position. However, other suitable drive arrangements are also contemplated, e.g., using cam pins and cam slots, a screw-drive mechanism, etc.

Regardless of the particular configuration of jaw member 110, jaw member 110 may include a longitudinally-extending insulative member 115 extending along at least a portion of the length of tissue-treating surface 114. Insulative member 115 may be transversely centered on tissue-treating surface 114 or may be offset relative thereto. Further, insulative member 115 may be disposed, e.g., deposited, coated, etc., on tissue-treating surface 114, may be positioned within a channel or recess defined within tissue-treating surface 114, or may define any other suitable configuration. Additionally, insulative member 115 may be substantially (within manufacturing, material, and/or use tolerances) coplanar with tissue-treating surface 114, may protrude from tissue-treating surface 114, may be recessed relative to tissue-treating surface 114, or may include different portions that are coplanar, protruding, and/or recessed relative to tissue-treating surface 114. Insulative member 115 may be formed from, for example, ceramic, parylene, nylon, PTFE, or other suitable material(s) (including combinations of insulative and non-insulative materials).

With reference to FIGS. 4 and 5B, as noted above, jaw member 120 includes a structural frame 121, a jaw housing 122, and a tissue-treating plate 123 defining the tissue-treating surface 124 thereof. Jaw member 120 further include a thermal cutting element 130. Structural frame 121 defines a proximal flange portion 126 and a distal body portion (not shown) extending distally from proximal flange portion 126. Proximal flange portion 126 is bifurcated to define a pair of spaced-apart proximal flange portion segments that receive proximal flange 111 of jaw member 110 therebetween and define aligned apertures 127 configured for receipt of pivot 103 therethrough to pivotably couple jaw members 110, 120 with one another.

Jaw housing 122 of jaw member 120 is disposed about the distal body portion of structural frame 121, e.g., via over-molding, adhesion, mechanical engagement, etc., and supports tissue-treating plate 123 thereon, e.g., via overmolding, adhesion, mechanical engagement, depositing (such as, for example, via sputtering), etc. Tissue-treating plate 123, as noted above, defines tissue-treating surface 124. A longitudinally-extending slot 125 is defined through tissue-treating plate 123 and is positioned to oppose insulative member 115 of jaw member 110 (FIG. 5A) in the approximated position. Slot 125 may extending through at least a portion of jaw housing 122, a jaw insert (if so provided), and/or other components of jaw member 120 to enable receipt of thermal cutting element 130 at least partially within slot 125.

Thermal cutting element 130, more specifically, is disposed within longitudinally-extending slot 125 such that thermal cutting element 130 opposes insulative member 115 of jaw member 110 (FIG. 5A) in the approximated position. Thermal cutting element 130 may be configured to contact insulative member 115 (FIG. 5A) in the approximated position to regulate or contribute to regulation of a gap distance between tissue-treating surfaces 114, 124 in the approximated position. Alternatively or additionally, one or more stop members (not shown) associated with jaw member 110 and/or jaw member 120 may be provided to regulate the gap distance between tissue-treating surfaces 114, 124 in the approximated position.

Thermal cutting element 130 may be surrounded by an insulative member 128 disposed within slot 125 to electrically isolate thermal cutting element from tissue-treating plate 123. Alternatively or additionally, thermal cutting element 130 may include an insulative coating on at least the sides thereof for similar purposes. Thermal cutting element 130 and insulative member 128 may similarly or differently be substantially (within manufacturing, material, and/or use tolerances) coplanar with tissue-treating surface 124, may protrude from tissue-treating surface 124, may be recessed relative to tissue-treating surface 124, or may include different portions that are coplanar, protruding, and/or recessed relative to tissue-treating surface 124.

In embodiments where end effector assembly 100, or a portion thereof, is curved, longitudinally-extending slot 125 and thermal cutting element 130 may similarly be curved, e.g., wherein longitudinally-extending slot 125 and thermal cutting element 130 (or corresponding portions thereof) are relatively configured with reference to an arc (or arcs) of curvature rather than a longitudinal axis. Thus, the terms longitudinal, transverse, and the like as utilized herein are not limited to linear configurations, e.g., along linear axes, but apply equally to curved configurations, e.g., along arcs of curvature. In such curved configurations, insulating member 115 of jaw member 110 (FIG. 5A) is likewise curved.

Generally referring to FIGS. 1-5B, tissue-treating plates 113, 123 are formed from an electrically conductive material, e.g., for conducting electrical energy therebetween for treating tissue, although tissue-treating plates 113, 123 may alternatively be configured to conduct any suitable energy, e.g., thermal, microwave, light, ultrasonic, etc., through tissue grasped therebetween for energy-based tissue treatment. As mentioned above, tissue-treating plates 113, 123 are coupled to activation switch 80 and electrosurgical generator "G" (FIG. 1) such that energy may be selectively supplied to tissue-treating plates 113, 123 and conducted therebetween and through tissue disposed between jaw members 110, 120 to treat tissue, e.g., seal tissue on either side and extending across thermal cutting element 130.

Thermal cutting element 130, on the other hand, is configured to connect to electrosurgical generator "G" (FIG. 1) and second activation switch 90 to enable selective activation of the supply of energy to thermal cutting element 130 for heating thermal cutting element 130 to thermally cut tissue disposed between jaw members 110, 120, e.g., to cut the sealed tissue into first and second sealed tissue portions. Other configurations including multi-mode switches, other separate switches, etc. may alternatively be provided.

Figure 6A:
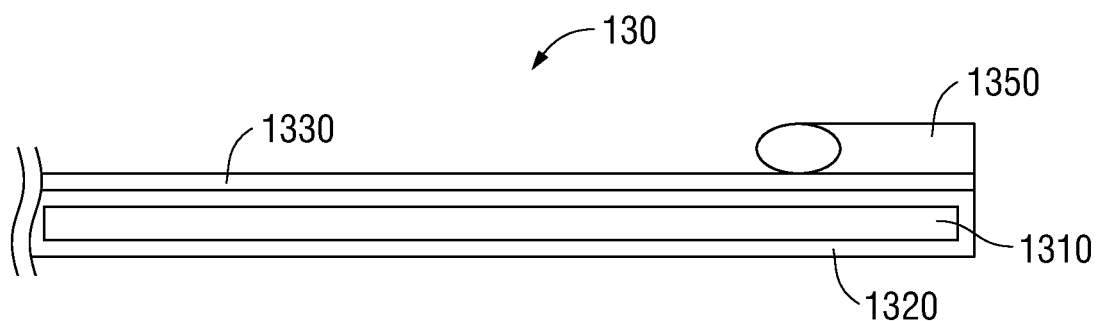
FIGS. 6A-6C are partial side, cross-sectional views of various configurations of thermal cutting elements provided in accordance with the present disclosure and configured for use with the second jaw member of the end effector assembly of FIG. 4.
Figure 6B:
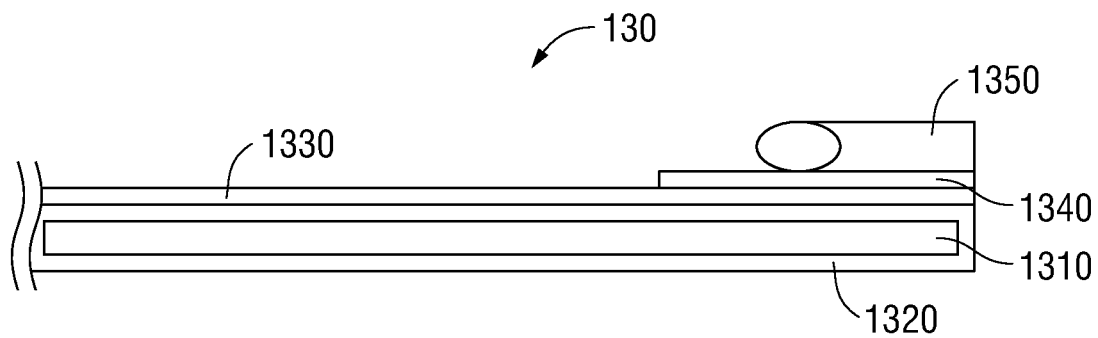
Figure 6C:
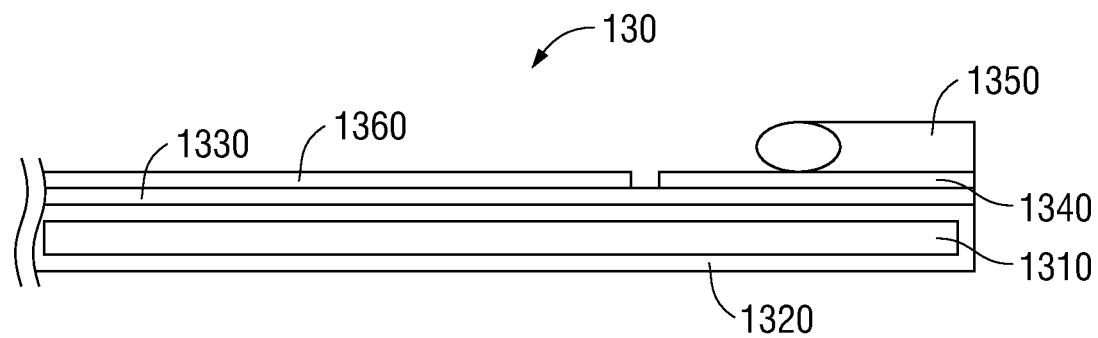

Referring to FIGS. 6A-6C, thermal cutting element 130 may be any suitable thermal cutting element such as, for example, an aluminum substrate at least a portion of which is Plasma Electrolytic Oxidation (PEO)-treated with a heating layer affixed thereto such that when an AC voltage is applied, the thermal cutting element 130 is heated for thermally cutting tissue in contact therewith. More specifically, thermal cutting element 130 may include a substrate 1310, a PEO coating 1320 surrounding at least a portion of the outer surface of substrate 1310, and a heating layer 1330 disposed on PEO coating 1320. Thermal cutting element 130, in embodiments, may further include first and second electrical contacts 1340 (only one electrical contact is illustrated in FIGS. 6B & 6C) disposed on heating layer 1330 for connection of first and second electrical lead wires 1350 thereto (only one electrical lead wire is illustrated in FIGS. 6A-6C), although electrical lead wires 1350 may alternatively be connected to heating layer 1330 without the use of electrical contacts (see FIG. 6A). Additionally or alternatively, thermal cutting element 130 may include an insulating layer 1360 (FIG. 6C) disposed on a portion of heating layer 1330 and/or PEO coating 1320. In embodiments, as an alternative to a PEO-coated substrate, a ceramic substrate may be utilized.

Figure 7:
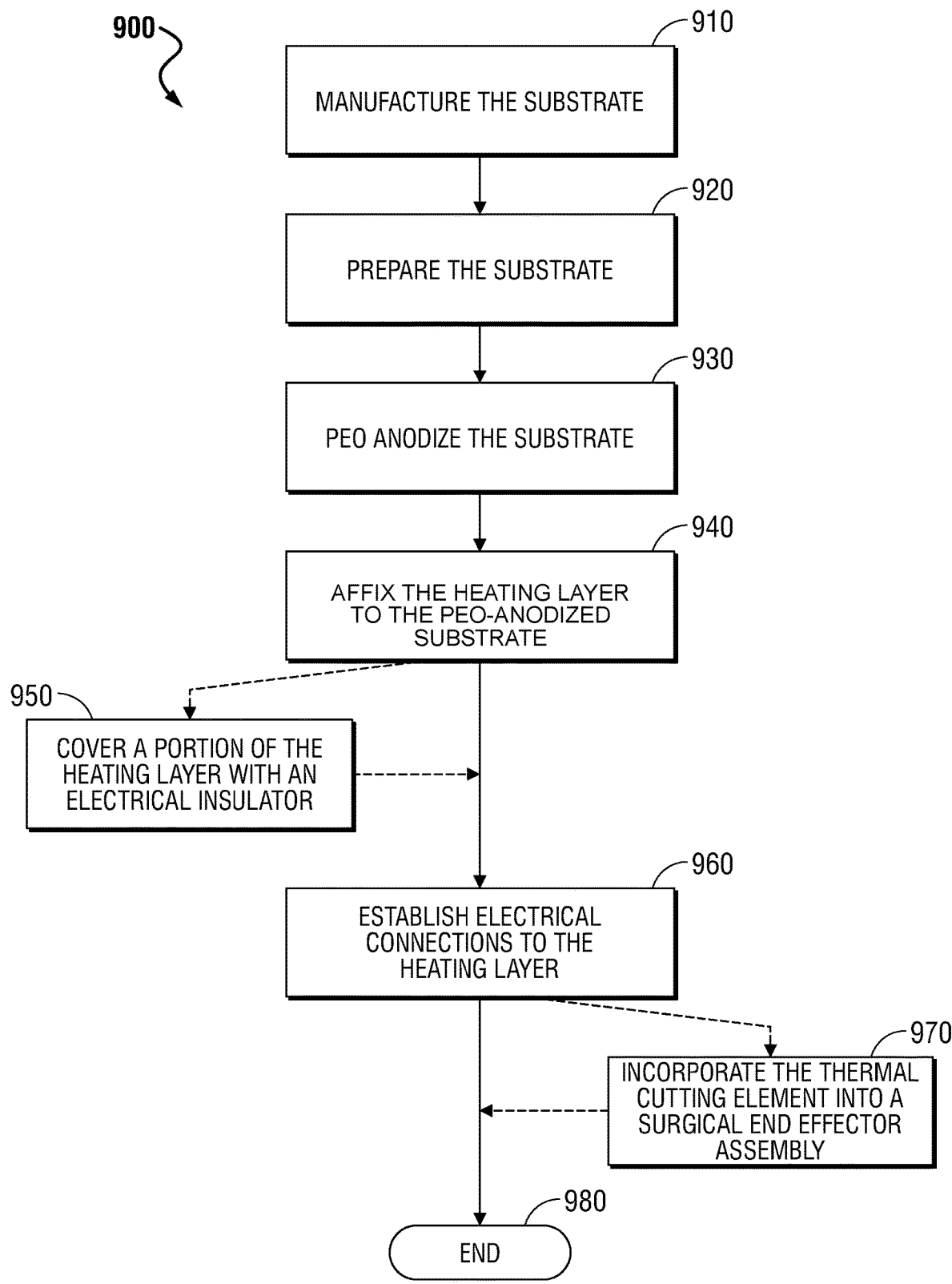
FIG. 7 is a flow diagram illustrating a method of manufacturing a thermal cutting element provided in accordance with the present disclosure.

Turning to FIG. 7, in conjunction with FIGS. 6A-6C, a method 900 of manufacturing thermal cutting element 130 is detailed. Initially, at step 910, substrate 1310 is manufactured. For the purposes herein, the term "manufacturing" includes obtaining a component from, for example, a third party vendor or vendors that manufactured the component. Further, although necessarily described hereinbelow in an order, the various steps of method 900, to the extent practicable, need not be perform in the order detailed below; simultaneous performance of multiple steps is also contemplated.

With respect to manufacturing substrate 1310 at step 910, substrate 1310 may be made from aluminum, titanium, alloys thereof, combinations thereof, or other suitable material(s) that can be PEO anodized. In embodiments, a plurality of substrates 1310 are manufactured together such as, for example, as progressive-die stamped parts on a carrier strip. In other embodiments, each substrate 1310 may be manufactured individually such as, for example, via machining, casting, forging, fine-blanking, or any other suitable method. For purposes of simplicity, method 900 is detailed below with respect to a single substrate 1310 and thermal cutting element 130, although it is understood that method 900 may similarly apply to a plurality of substrates 1310 for forming a plurality of thermal cutting elements 130.

Continuing to step 920, substrate 1310 is prepared. Preparing substrate 1310 may include degreasing and/or cleaning, e.g., using any suitable methods; deburring; edge-breaking; and/or surface modifications such as one or more of tumbling, grit blasting, chemical etching, electropolishing, etc.

Once substrate 1310 is prepared, substrate 1310 is PEO anodized at step 930. More specifically, in order to PEO anodize substrate 1310, substrate 1310 is utilized as an anode in an electrochemical bath. That is, substrate 1310 is immersed in a chilled bath of electrolyte which consists of a dilute alkaline solution, e.g., containing Sodium or Potassium Silicate. Substrate 1310 is connected to an electrical energy source to define one of the electrodes in the electrochemical bath, with a counter-electrode, e.g., made from an inert material such as stainless steel, also electrically coupled to the electrochemical bath, e.g., forming the wall of the bath itself. Electrical potentials, e.g., in embodiments, of over 200V and up to 700V, are applied between the two electrodes. The potentials may be continuous or pulsed direct current (DC) or pulses of alternating current (AC). The desired resultant thickness of PEO coating 1320 may dictate the particular voltage applied and/or the time that substrate 1310 remains in the bath.

Higher voltage potentials are applied for PEO anodization as compared to standard anodization. For example, in embodiments, e.g., with respect to PEO anodization of aluminum, the voltage potentials may be at least 200V and up to 700V. These high voltages exceed the dielectric breakdown potential of the growing oxide film and allow discharges. These discharges result in localized plasma reactions, with conditions of high temperature and pressure, which modify the growing oxide, e.g., via melting, melt-flow, re-solidification, sintering and/or densification of the growing oxide. In particular, the oxide is partially converted from amorphous alumina into crystalline forms such as corundum ($\alpha$-Al2O3) which has increased hardness.

Once PEO anodization of substrate 1310 at step 930 is completed to form PEO coating 1320 about at least a portion of substrate 1310, the coated substrate may be washed with water. Additionally or alternatively, in embodiments, the coated substrate may be polished to eliminate or reduce surface roughening resulting from the PEO process.

The PEO anodization process of step 930 may be controlled such that coating 1320 defines an average thickness, in embodiments, of about 50 micrometers to about 150 micrometers; in other embodiments, about 75 micrometers to about 125 micrometers; in still other embodiments, about 90 micrometers to about 110 micrometers; and, in yet other embodiments, about 100 micrometers. "About" as utilized herein takes into account material, manufacturing, measurement, environment, and other tolerances generally acceptable for the particular application and may include at least +/−10% variation.

The electrical insulation properties of a PEO coating 1320 such as detailed above are at least about 10V per micrometer. Thus, for a PEO coating 1320 having a thickness of about 100 micrometers, the PEO coating 1320 provides a dielectric barrier of at least 1000V. This allows PEO coating 1320 to withstand temperatures of up to 1000° C. and is advantageous compared to standard anodization which cannot withstand temperatures above about 150° C. without cracking.

Once PEO coating 1320 is formed about substrate 1310 as detailed above, heating layer 1330 may be affixed to the PEO-coated substrate, as indicated as step 940. With respect to affixing heating layer 1330, this may be accomplished via a deposition process such as sputtering, although other methods of affixing heating layer 1330 are also contemplated such as, for example, screen printing. These methods are advantageous in that they allows for affixation without requiring substrate 1310 to be heated above its melting point. Heating layer 1330 may be formed from, for example, nichrome, kanthal, platinum, combinations thereof, or other suitable metal(s) meeting desired heating and electrical resistance characteristics, e.g., positive thermal coefficient (PTC) resistive heating materials.

The sputtering process, more specifically, may include loading the coated substrate into a shadow mask fixture and sputtering the heating layer 1330 onto the coated substrate to affix a heating element circuit onto the PEO-coated substrate.

The screen printing process, more specifically, may include loading the coated substrate into a screen printing fixture and screen printing the heating layer 1330, along with a binder, onto the coated substrate. The result is then fired at about 850° C. to about 1000° C. to burn off the binder and sinter the heating layer 1330 to the PEO-coated substrate, thereby affixing a heating element circuit onto the PEO-coated substrate.

In embodiments, at step 950, an electrically insulative material is disposed about the heating layer 1330 to form an insulating layer 1360. The insulating layer 1360 may be silica and/or sputtered onto the heating layer 1330 to provide oxidation and/or fluid ingress protection as well as electrical insulation. Alternatively, the insulating layer 1360 may be glass and/or screen printed and fired over the heating layer 1330 to provide oxidation and/or fluid ingress protection as well as electrical insulation. Other suitable materials and/or methods of affixation are also contemplated.

As indicated at step 960, electrical connections to heating layer 1330 are established. In embodiments, electrical contacts 1340 are affixed to heating layer 1330 for connection of corresponding electrical lead wires 1350 thereto. Alternatively, electrical lead wires 1350 may be connected to heating layer 1330 without use of electrical contacts 1340.

The electrical contacts 1340, in embodiments where provided, may be formed from, for example, a material suitable for facilitating electrical connection, e.g., nickel or copper. Electrical contacts 1340 may be applied at end portions of the heating element circuit via sputtering, e.g., utilizing a second shadow mask fixture. In embodiments, the electrical contacts 1340 may be thickened using electroplating, e.g., of nickel or other suitable electroplateable metal. As an alternative to sputtering, electrical contacts 1340 in the form of electrical contact pads may be screen printed and fired onto end portions of the heating element circuit.

Electrical lead wires 1350 are connected, directly or indirectly, to the electrical contacts 1340 or the end portions of the heating element circuit via sputtering (in embodiments where electrical contacts 1340 are not provided).

Electrical lead wires 1350 may be connected using mechanical connectors, e.g., spring clips 2370 (See FIG. 9), or other suitable methods of attachment, e.g., resistance welding, laser welding, ball bonding, electroplating, brazing, soldering, using electrically-conductive adhesives, etc.

The formed thermal cutting element 130 may finally be integrated, attached, or otherwise incorporated into a surgical end effector assembly, e.g., end effector assemblies 100, 2100 (FIGS. 4 and 9, respectively), as indicated at step 970. Otherwise or thereafter, the method ends at 980.

Figure 8A:
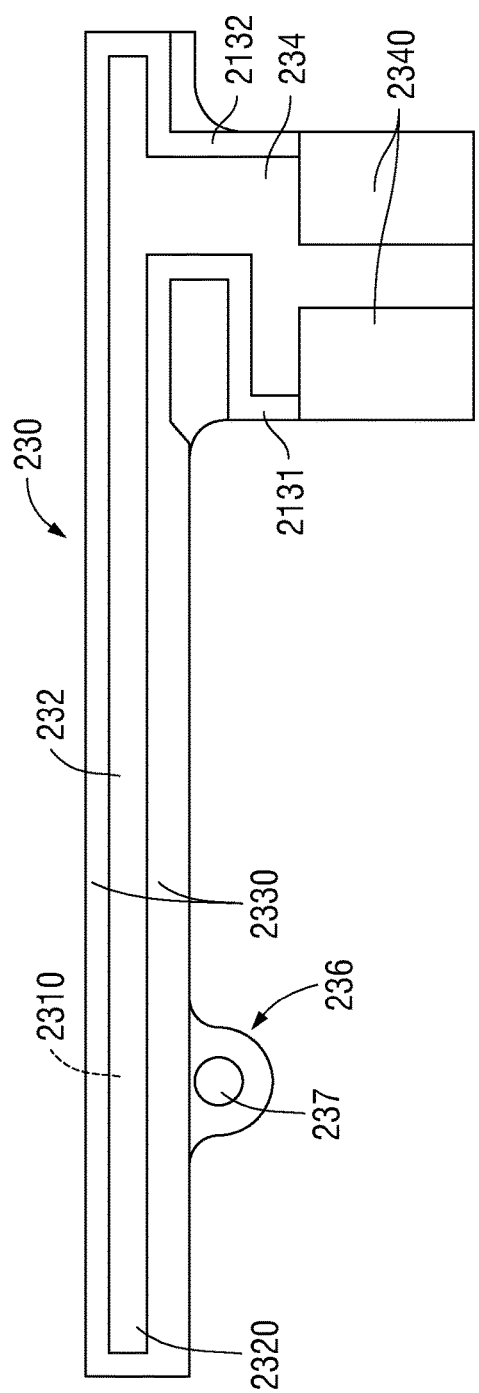
FIG. 8A is a side view of another thermal cutting element provided in accordance with the present disclosure.
Figure 8B:
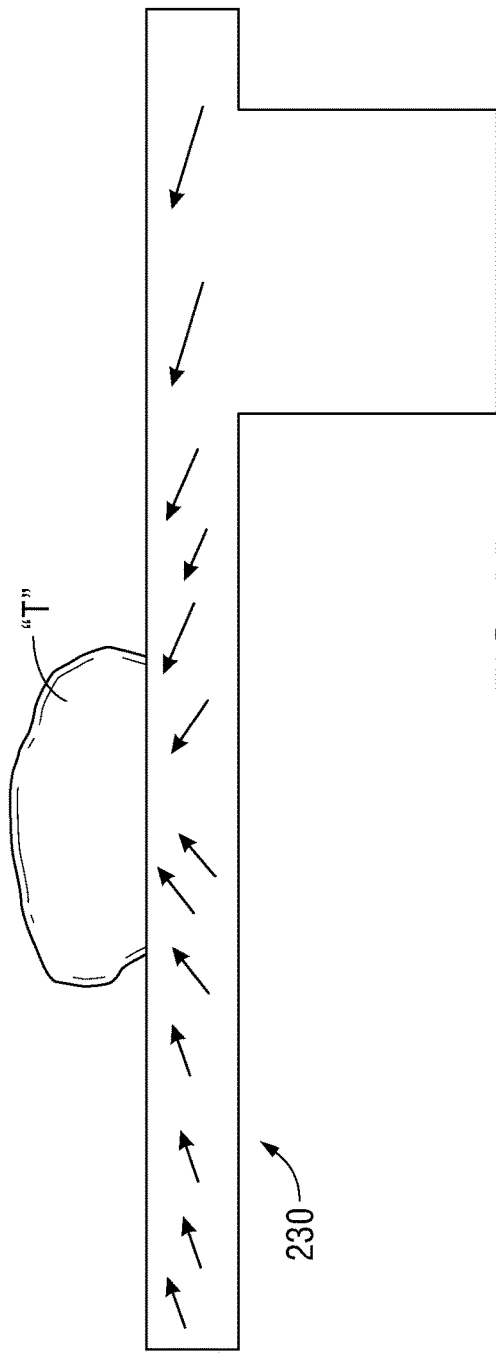
FIG. 8B is a side view illustrating the thermal cutting element of FIG. 8A in use applying thermal energy to tissue.

With reference to FIGS. 8A and 8B, and initially to FIG. 8A, an embodiment of a thermal cutting element 230 in accordance with the present disclosure is illustrated, e.g., manufactured utilizing the above-detailed method 900 (FIG. 7) or manufactured in any other other suitable manner. Thermal cutting element 230 includes a substrate 2310, a PEO coating 2320 disposed about substrate 2310, a heating layer 2330 disposed on the PEO coating 2320 to form a heating element circuit including first and second end portions 2331, 2332, and first and second contacts 2340 electrically coupled to the respective first and second end portions 2331, 2332 of heating layer 2330. Thermal cutting element 230 defines an elongated body 232, a proximal connection flange 234 extending from a proximal end portion of elongated body 232, and one or more attachment flanges 236 extending from elongated body 232, e.g., from a central or distal end portion of elongated body 232. First and second end portions 2331, 2332 of heating layer 2330 are disposed at proximal connection flange 234. Heating layer 2330 defines a continuous circuit trace including first and second spaced-apart segments extending from first and second end portions 2331, 2332, respectively, distally along elongated body 232 to or adjacent a distal end portion of elongated body 232, wherein the first and second segments are interconnected with one another via a connector segment of heating layer 2330.

First and second contacts 2340 are affixed to first and second end portions 2331, 2332, respectively, of heating layer 2330 at proximal connection flange 234 to enable connection of electrical lead wires thereto for applying an AC voltage thereto to heat thermal cutting element 230. In embodiments, proximal connection flange 234 extends orthogonally relative to a longitudinal axis of elongated body 232, although other configurations are also contemplated.

Attachment flange 236 defines an aperture 237 configured to facilitate engagement of thermal cutting element 230 within a jaw member e.g., jaw member 2120 (FIG. 9), or other suitable component of a surgical end effector assembly. In embodiments, attachment flange 236 extends orthogonally relative to a longitudinal axis of elongated body 232, although other configurations are also contemplated.

FIG. 8B illustrates thermal cutting element 230 in use, wherein tissue "T" is in contact with thermal cutting element 230 and an AC voltage is applied across first and second contacts 2340 to thereby heat thermal cutting element 230. The directional arrows are indicative of a thermal gradient whereby, as a result of the configuration of thermal cutting element 230, heat is conducted from portions of thermal cutting element 230 not in contact with tissue "T" to those portions that are in contact with tissue "T." This facilitates heating and controlling the temperature of the portion of thermal cutting element 230 that is in contact with tissue "T," thus facilitating controlling the cutting of tissue "T."

Figure 9:
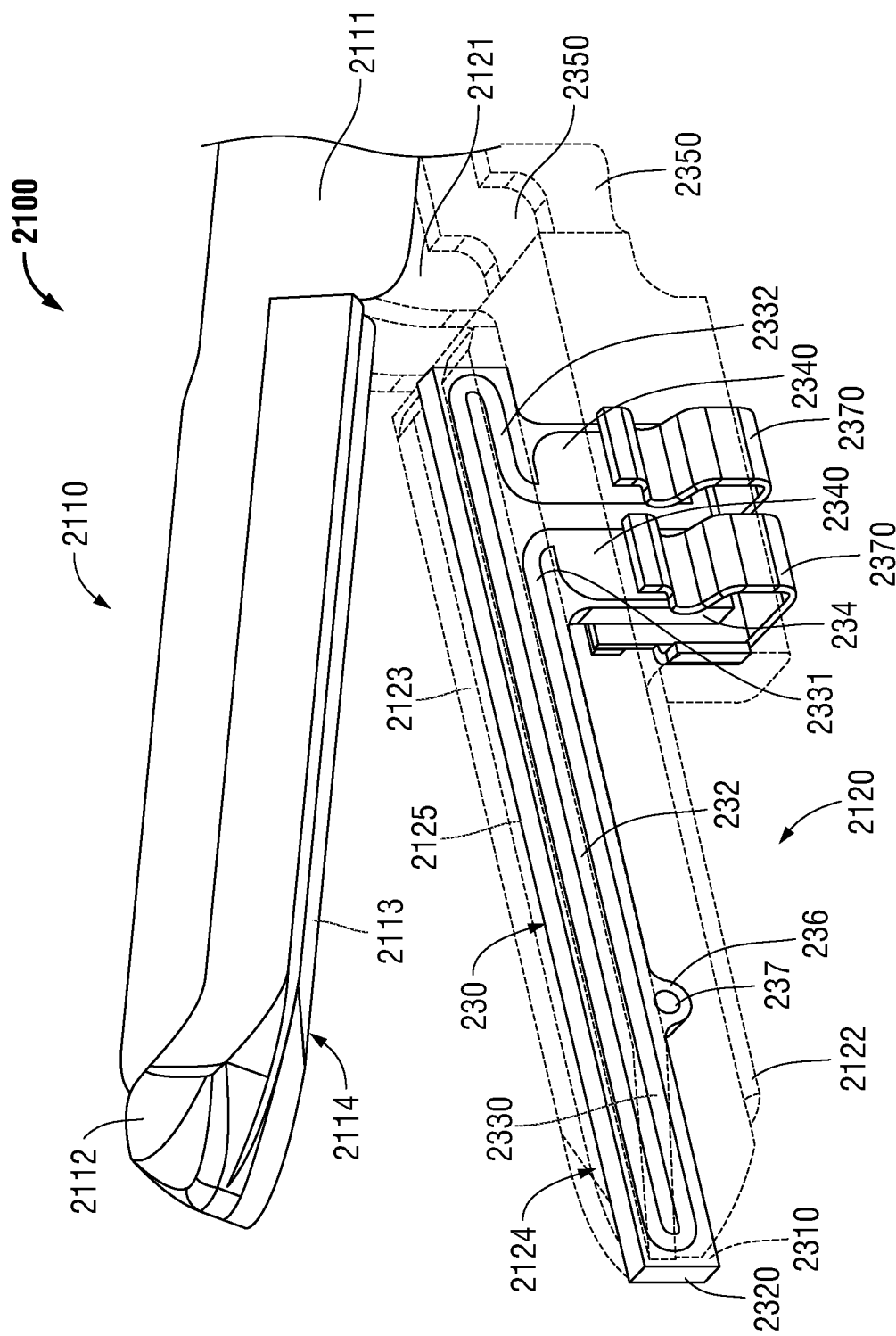
FIG. 9 is a perspective, partial see-through view of an end effector assembly provided in accordance with the present disclosure incorporating the thermal cutting element of FIG. 8A therein.

Turning to FIG. 9, thermal cutting element 230 (FIGS. 8A and 8B) is shown incorporated into an end effector assembly 2100 similar to end effector assembly 100 (FIG. 4). End effector assembly 2100 generally includes first and second jaw members 2110, 2120 at least one of which is movable relative to the other between spaced-apart and approximated positions. Each jaw member 2110, 2120 includes a structural frame 2111, 2121, a jaw housing 2112, 2122, and a tissue-treating plate 2113, 2123 defining a tissue-treating surface 2114, 2124. End effector assembly 2100 may further include any of the features of end effector assembly 100 (FIG. 4) as detailed above and may operate in a similar manner. Thus, only differences are described in detail below for purposes of brevity.

Jaw member 2120 includes first and second spring clips 2370 disposed therein and first and second electrical lead wires 2350 connected to respective first and second spring clips 2370. Thermal cutting element 230 is seated within a longitudinally-extending slot 2125 defined within jaw member 2120 such that respective first and second spring clips 2370 engage proximal connection flange 234 and are biased to maintain electrical contact with electrical contacts 2340, thus electrically connecting electrical lead wires 2350 with heating layer 2330. Elongated body 232 of thermal cutting element 230 extends longitudinally along jaw member 210 and is positioned flush with, recessed relative to, or protruding from tissue-treating surface 2124. Elongated body 232 may terminate prior to, may extend to, or may extend beyond a distal end of tissue-treating plate 2123 and/or jaw member 2120.

Thermal cutting element 230 may be secured within jaw member 2120 via an internal jaw insert (not shown) and/or overmolding of jaw housing 2122 about structural frame 2121. With respect to overmolding jaw housing 2122 (or an internal jaw insert), aperture 237 of attachment flange 236 enables overmold material to flow therethrough, thus facilitating secure engagement. Engagement of proximal connection flange 234 with spring clips 2370 also facilitates mechanical securement of thermal cutting element 230 in position.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of manufacturing a thermal cutting element for a surgical instrument, the method comprising:
   manufacturing a substrate;
   coating at least a portion of the substrate via Plasma Electrolytic Oxidation (PEO); and
   disposing a heating element on at least a portion of the PEO-coated substrate, wherein disposing the heating element includes sputtering the heating element onto the PEO-coated substrate.

2. The method according to claim 1, wherein disposing the heating element includes forming a continuous circuit trace on the PEO-coated substrate, the continuous circuit trace extending between first and second end portions of the heating element.

3. The method according to claim 2, wherein forming the continuous circuit trace on the PEO-coated substrate includes forming a circuit trace pattern wherein first and second end portions of the circuit trace pattern are disposed adjacent one another.

4. The method according to claim 1, wherein disposing the heating element includes screen printing the heating element onto the PEO-coated substrate.

5. Method according to claim 1, further comprising:
disposing first and second electrical contacts on respective first and second end portions of the heating element.

6. The method according to claim 5, wherein disposing the first and second electrical contacts includes sputtering the first and second electrical contacts onto the respective first and second end portions of the heating element.

7. The method according to claim 5, wherein disposing the first and second electrical contacts includes screen printing the first and second electrical contacts onto the respective first and second end portions of the heating element.

8. The method according to claim 1, wherein manufacturing the substrate includes die-stamping the substrate.

9. The method according to claim 8, wherein the substrate is one of a plurality of substrates progressively-die stamped from a carrier strip.

10. The method according to claim 1, further comprising disposing an electrically insulative material on at least a portion of the heating element.

11. Method according to claim 1, wherein the PEO is controlled such that the PEO coating defines an average thickness of about 50 micrometers to about 150 micrometers.

12. The method according to claim 1, wherein the PEO is controlled such that the PEO coating defines an average thickness of about 75 micrometers to about 125 micrometers.

13. Method according to claim 1, wherein the PEO is controlled such that the PEO coating defines an average thickness of about 100 micrometers.

14. The method according to claim 1, further comprising:
attaching the heating element-disposed, PEO-coated substrate to a jaw member.

15. The method according to claim 14, wherein attaching includes:
electrically coupling first and second end portions of the heating element to first and second electrical connectors, respectively.

16. The method according to claim 14, wherein attaching includes:
mechanically coupling an attachment flange of the substrate to a jaw housing of the jaw member.

17. The method according to claim 16, wherein mechanically coupling includes overmolding the jaw housing to the attachment flange.

18. A method of manufacturing a thermal cutting element for a surgical instrument, the method comprising:
manufacturing a substrate;
coating at least a portion of the substrate via Plasma Electrolytic Oxidation (PEO); and
disposing a heating element on at least a portion of the PEO-coated substrate, wherein disposing the heating element includes screen printing the heating element onto the PEO-coated substrate.

19. A method of manufacturing a thermal cutting element for a surgical instrument, the method comprising:
manufacturing a substrate;
coating at least a portion of the substrate via Plasma Electrolytic Oxidation (PEO);
disposing a heating element on at least a portion of the PEO-coated substrate; and
disposing first and second electrical contacts on respective first and second end portions of the heating element, wherein the disposing of the first and second electrical contacts includes sputtering the first and second electrical contacts onto the respective first and second end portions of the heating element.

20. A method of manufacturing a thermal cutting element for a surgical instrument, the method comprising:
manufacturing a substrate;
coating at least a portion of the substrate via Plasma Electrolytic Oxidation (PEO);
disposing a heating element on at least a portion of the PEO-coated substrate; and
disposing first and second electrical contacts on respective first and second end portions of the heating element, wherein the disposing of the first and second electrical contacts includes screen printing the first and second electrical contacts onto the respective first and second end portions of the heating element.

* * * * *